United States Patent
Hete et al.

(10) Patent No.: US 10,821,245 B2
(45) Date of Patent: Nov. 3, 2020

(54) PRESSURE SUPPORT SYSTEM FOR BREATH STACKING THERAPY

(71) Applicant: KONINKLIJKE PHILIPS N.V., Eindhoven (NL)

(72) Inventors: Bernard F. Hete, Kittanning, PA (US); William Anthony Truschel, Oakmont, PA (US)

(73) Assignee: Koninklijke Philips N.V., Eindhoven (NL)

(*) Notice: Subject to any disclaimer, the term of this patent is extended or adjusted under 35 U.S.C. 154(b) by 938 days.

(21) Appl. No.: 14/889,459

(22) PCT Filed: May 6, 2014

(86) PCT No.: PCT/IB2014/061229
§ 371 (c)(1),
(2) Date: Nov. 6, 2015

(87) PCT Pub. No.: WO2014/181244
PCT Pub. Date: Nov. 13, 2014

(65) Prior Publication Data
US 2016/0089509 A1 Mar. 31, 2016

Related U.S. Application Data

(60) Provisional application No. 61/820,997, filed on May 8, 2013.

(51) Int. Cl.
*A61M 16/00* (2006.01)
*A61M 16/20* (2006.01)
*A61M 16/16* (2006.01)

(52) U.S. Cl.
CPC ...... *A61M 16/024* (2017.08); *A61M 16/0057* (2013.01); *A61M 16/0069* (2014.02);
(Continued)

(58) Field of Classification Search
CPC .............. A61M 16/024; A61M 16/022; A61M 16/021; A61M 16/026; A61M 2016/0027;
(Continued)

(56) References Cited

U.S. PATENT DOCUMENTS 5,752,509 A * 5/1998 Lachmann .......... A61M 16/024
128/203.12
6,467,477 B1 * 10/2002 Frank .................. A61M 16/024
128/203.23
(Continued)

FOREIGN PATENT DOCUMENTS

| CN | 101622036 A | 1/2010 |
|---|---|---|
| CN | 102405075 A | 4/2012 |
| JP | 2010517701 A | 5/2010 |
| JP | 2012520718 A | 9/2012 |
| WO | WO2008126082 A1 | 10/2008 |

*Primary Examiner* — Colin W Stuart
*Assistant Examiner* — Douglas Y Sul
(74) *Attorney, Agent, or Firm* — Daniel H. Brean

(57) ABSTRACT

The present disclosure pertains to a pressure support system (10) configured to deliver a pressurized flow of breathable gas to the airway of a subject (12), the pressure support system comprising: a pressure generator (14) configured to generate the pressurized flow of breathable gas; one or more sensors (18) configured to generate output signals conveying information related to whether the subject is ready to receive breath stacking therapy; and one or more processors (20) configured to execute computer program modules, the computer program modules comprising: —a control module (52) configured to control the pressure generator to generate the pressurized flow of breathable gas according to a pressure control therapy regime, —an event module (54) configured to determine breath stacking events responsive to the output signals indicating that the subject is ready to receive breath stacking therapy, and —a breath stacking module (56) configured to, responsive to the determination of a breath
(Continued)

stacking event, control the pressure generator to generate the pressurized flow of breathable gas according to a breath stacking therapy regime.

9 Claims, 4 Drawing Sheets

(52) U.S. Cl.
CPC ......... *A61M 16/161* (2014.02); *A61M 16/202* (2014.02); *A61M 2016/0027* (2013.01); *A61M 2016/0036* (2013.01); *A61M 2205/3331* (2013.01); *A61M 2205/3365* (2013.01); *A61M 2205/3368* (2013.01); *A61M 2205/3375* (2013.01); *A61M 2205/3569* (2013.01); *A61M 2205/3592* (2013.01); *A61M 2205/505* (2013.01); *A61M 2205/52* (2013.01); *A61M 2230/40* (2013.01); *A61M 2230/63* (2013.01)

(58) Field of Classification Search
CPC .... A61M 2016/003; A61M 2016/0036; A61M 2205/3331; A61M 2231/40
See application file for complete search history.

(56) References Cited

U.S. PATENT DOCUMENTS

| | | |
|---|---|---|
| 8,789,528 B2 | 7/2014 | Carter |
| 9,833,583 B2 | 12/2017 | Pittman |
| 2006/0070624 A1* | 4/2006 | Kane .................... A61M 16/00 128/204.23 |
| 2006/0249149 A1 | 11/2006 | Meier |
| 2008/0092894 A1 | 4/2008 | Nicolazzi |
| 2008/0110451 A1 | 5/2008 | Dunsmore |
| 2008/0202525 A1 | 8/2008 | Mitton |
| 2008/0202528 A1* | 8/2008 | Carter .............. A61M 16/0051 128/204.23 |
| 2009/0078255 A1 | 3/2009 | Bowman |
| 2010/0095964 A1* | 4/2010 | Tham .................... A61B 5/022 128/204.23 |
| 2012/0003620 A1* | 1/2012 | Pittman ................. A61M 16/00 434/262 |
| 2012/0138057 A1* | 6/2012 | Tham ................. A61M 16/024 128/204.23 |

* cited by examiner

PRESSURE SUPPORT SYSTEM FOR BREATH STACKING THERAPY

This patent application claims the priority benefit under 35 U.S.C. § 371 of international patent application no. PCT/IB2014/061229, filed May 6, 2014, which claims the priority benefit under 35 U.S.C. § 119(e) of U.S. Provisional Application No. 61/820,997 filed on May 8, 2013, the contents of which are herein incorporated by reference.

BACKGROUND OF THE INVENTION

1. Field of the Invention

The present disclosure pertains to a pressure support system configured to deliver a pressurized flow of breathable gas to the airway of a subject.

2. Description of the Related Art

Breath stacking therapy during volume control ventilation is known. Breath stacking has many known physical benefits. For example, breath stacking improves alveolar ventilation in a patient. A regimen of breath stacking prevents the undergrowth of the thoracic rib cage in pediatric neuromuscular disease patients, exercises the range of motion of skeletal articulations in adult ventilator patients, and prevents the loss of maximum insufflation capacity for predicted inhalation or cough effectiveness. There is no mechanism for breath stacking therapy for patients and/or clinicians who prefer pressure controlled ventilation.

SUMMARY

Accordingly, one or more aspects of the present disclosure relate to a pressure support system configured to deliver a pressurized flow of breathable gas to the airway of a subject. The pressure support system comprises a pressure generator, one or more sensors, one or more processors, and/or other components. The pressure generator is configured to generate the pressurized flow of breathable gas. The one or more sensors are configured to generate output signals conveying information related to whether the subject is ready to receive breath stacking therapy. The one or more processors are configured to execute computer program modules. The computer program modules comprise a control module, an event module, a breath stacking module, and/or other modules. The control module is configured to control the pressure generator to generate the pressurized flow of breathable gas according to a pressure control therapy regime. The event module is configured to determine breath stacking events responsive to the output signals indicating that the subject is ready to receive breath stacking therapy. The breath stacking module is configured to, responsive to the determination of a breath stacking event, control the pressure generator to generate the pressurized flow of breathable gas according to a breath stacking therapy regime.

Yet another aspect of the present disclosure relates to a method of delivering a pressurized flow of breathable gas to the airway of a subject with a pressure support system. The pressure support system comprises a pressure generator, one or more sensors, one or more processors, and/or other components. The one or more processors are configured to execute computer program modules. The computer program modules comprise a control module, an event module, a breath stacking module, and/or other modules. The method comprises generating the pressurized flow of breathable gas with the pressure generator; generating, with the one or more sensors, output signals conveying information related to whether the subject is ready to receive breath stacking therapy; controlling, with the control module, the pressure generator to generate the pressurized flow of breathable gas according to a pressure control therapy regime; determining, with the event module, breath stacking events responsive to the output signals indicating that the subject is ready to receive breath stacking therapy; and, responsive to the determination of a breath stacking event, controlling the pressure generator, with the breath stacking module, to generate the pressurized flow of breathable gas according to a breath stacking therapy regime.

Still another aspect of the present disclosure relates to a pressure support system configured to deliver a pressurized flow of breathable gas to the airway of a subject. The pressure support system comprises means for generating the pressurized flow of breathable gas; means for generating output signals conveying information related to whether the subject is ready to receive breath stacking therapy; means for controlling the means for generating the pressurized flow of breathable gas to generate the pressurized flow of breathable gas according to a pressure control therapy regime; means for determining breath stacking events responsive to the output signals indicating that the subject is ready to receive breath stacking therapy; and, responsive to the determination of a breath stacking event, means for controlling the means for generating the pressurized flow of breathable gas to generate the pressurized flow of breathable gas according to a breath stacking therapy regime.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
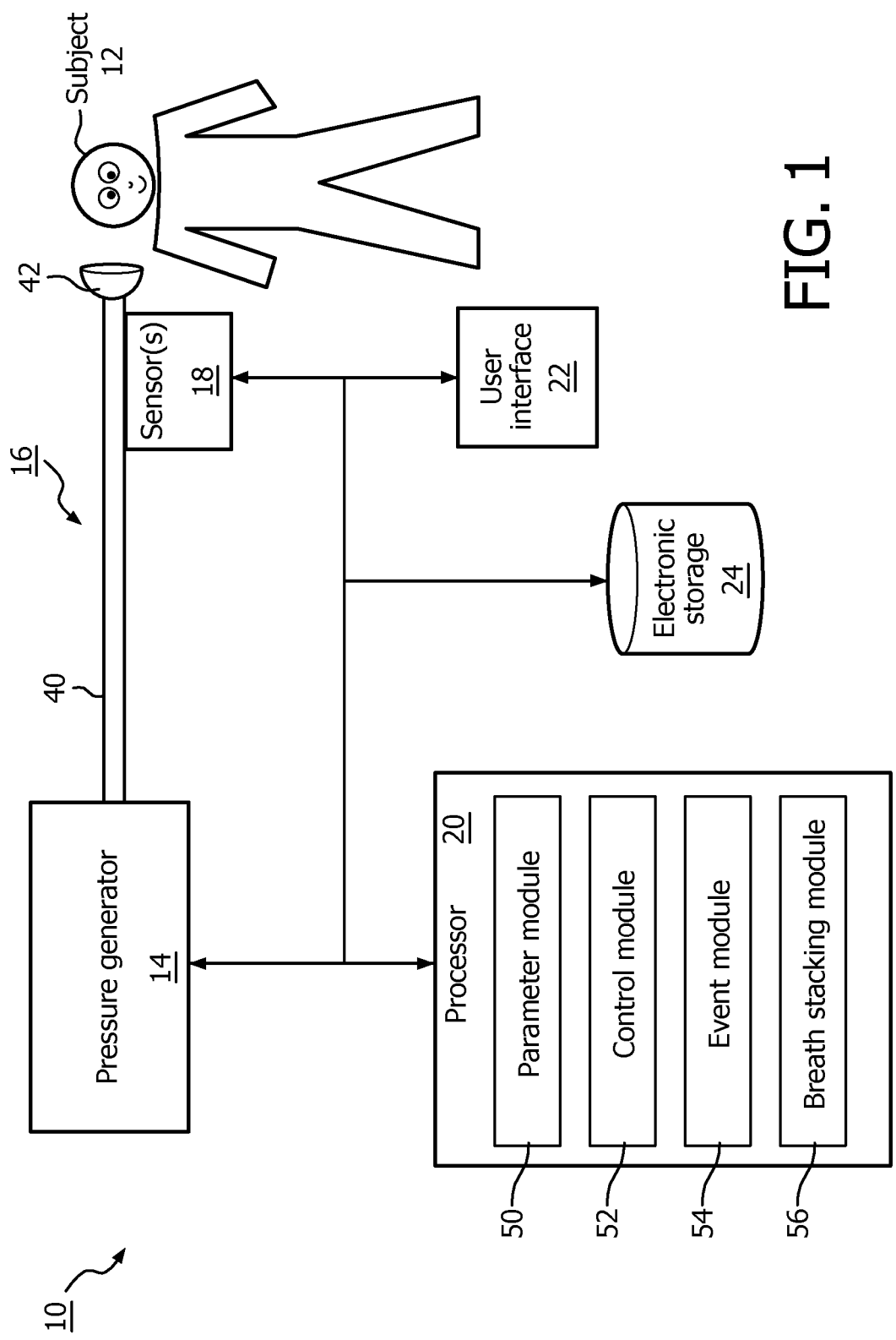
FIG. 1 is a schematic illustration of a pressure support system configured to deliver a pressurized flow of breathable gas to the airway of a subject.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates a pressure support system 10 configured to provide pressure support therapy to a subject 12. Pressure support system 10 is configured to provide the pressure support therapy in the form of a pressurized flow of breathable gas that is delivered to the airway of subject 12. Pressure support system 10 is configured to provide breath stacking therapy to subject 12 during pressure control ventilation. Breath stacking therapy allows a ventilated patient to accumulate the breathable gas in his or her airway during successive inhalations with partial and/or no exhalations between the successive inhalations. During breath stacking therapy, system 10 is configured to provide the pressurized flow of breathable gas at a pressure that is higher than the pressure provided during the normal course of pressure control ventilation. In some embodiments, system 10 provides a predetermined volume of the breathable gas to subject 12 during breath stacking therapy.

For example, system 10 may be configured to allow a constant pressure change on each successive breath, and/or a ramp in which the first pressure change steps are large and get smaller as each successive breath is stacked. As another example, system 10 may be configured such that, using one of a number of methods to assess lung compliance, the pressure increase may target a given volume based on the compliance. As a third example, system 10 may provide increasing pressure monitoring tidal volume until a set tidal volume is reached. This method effectively mimics breath stacking in a volume control mode while breath stacking is enabled, and returns to pressure support ventilation immediately after the breath stacking is complete.

In some embodiments, breath stacking may be titrated via an external measuring device that may be used to provide feedback for executing a stack, either through direct device control, and/or as an indication to the patient to trigger the event. An example of such a measurement may be end-tidal CO2]. System 10 is configured to determine whether subject 12 is ready for breath stacking therapy and deliver the increased pressure and/or the volume of gas during an inhalation of subject 12 immediately following a breath stacking readiness determination. In some embodiments, system 10 comprises one or more of a pressure generator 14, a subject interface 16, one or more sensors 18, one or more processors 20, a user interface 22, electronic storage 24, and/or other components.

Pressure generator 14 is configured to generate a flow of gas for delivery to the airway of a subject 12. Pressure generator 14 may control one or more parameters of the flow of gas (e.g., flow rate, pressure, volume, temperature, gas composition, etc.) for therapeutic purposes, and/or for other purposes. By way of a non-limiting example, pressure generator 14 may be configured to control the pressure and/or the volume of the flow of gas to the airway of subject 12.

Pressure generator 14 receives a flow of gas from a gas source (e.g., the ambient atmosphere), and elevates the pressure of that gas for delivery to the airway of subject 12. In some embodiments, pressure generator 14 receives a flow of gas from a gas source through an inlet port. Pressure generator 14 is any device, such as, for example, a pump, blower, piston, or bellows, that is capable of elevating the pressure of the received gas for delivery to a patient. Pressure generator 14 may comprise one or more valves for controlling the pressure/flow of gas. The present disclosure also contemplates controlling the operating speed of the blower, either alone or in combination with such valves, to control the pressure/flow of gas provided to subject 12.

Subject interface 16 is configured to communicate the pressurized flow of breathable gas to the airway of subject 12. As such, subject interface 16 comprises conduit 40, interface appliance 42, and/or other components. Conduit 40 is configured to convey the pressurized flow of gas to interface appliance 42. Conduit 40 may be a flexible length of hose, and/or other conduit that places interface appliance 42 in fluid communication with pressure generator 14. Interface appliance 42 is configured to deliver the flow of gas to the airway of subject 12. Interface appliance 42 places conduit 40 in communication with the airway of subject 12. In some embodiments, interface appliance 42 is configured to be non-invasively engaged by subject 12. Non-invasive engagement comprises removably engaging one or more external orifices of the airway of subject 12 (e.g., nostrils and/or mouth) to communicate gas between the airway of subject 12 and interface appliance 42.

Some examples of non-invasive interface appliance 42 may comprise, for example, a nasal cannula, a nasal mask, a nasal/oral mask, a full face mask, a total face mask, a mouthpiece, a "sipping" straw, the open end of a patient circuit tube, and/or other interface appliances that communicate a flow of gas with an airway of a subject. The present disclosure is not limited to these examples, and contemplates delivery of the flow of gas to the subject using any interface appliance, including an invasive interface appliance such as an endotracheal tube and/or other appliances. In some embodiments, interface appliance 42 is removably coupled to conduit 40. Interface appliance 42 may be removed for cleaning and/or for other purposes.

One or more sensors 18 are configured to generate output signals conveying information related to whether subject 12 is ready to receive breath stacking therapy. The one or more sensors 18 may be configured such that the output signals conveying information related to whether subject 12 is ready to receive breath stacking therapy include output signals conveying information related to one or more parameters of the gas within system 10. The one or more parameters of the gas within system 10 may comprise gas parameters related to the pressurized flow of breathable gas, breathing parameters related to respiration of subject 12, and/or other parameters.

The one or more gas parameters of the pressurized flow of breathable gas may comprise, for example, one or more of a pressure, a flow rate, a volume, humidity, temperature, acceleration, velocity, and/or other gas parameters. Breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters.

Sensors 18 may comprise one or more sensors that measure such parameters directly (e.g., through fluid communication with the flow of gas in interface appliance 42). Sensors 18 may comprise one or more sensors that generate output signals related to the one or more parameters indirectly. For example, sensors 18 may comprise one or more sensors configured to generate an output based on an operating parameter of pressure generator 14 (e.g., flow rate, volume, and/or pressure estimations from motor current, voltage, rotational velocity, and/or other operating parameters), and/or other sensors.

In some embodiments, sensors 18 include a readiness indicator device configured to receive an indication from subject 12 that he or she is ready to receive breath stacking therapy. The readiness indicator device may include, for example, a button, a switch, a camera, a microphone, a motion sensing device (e.g., subject 12 may wave to indicate readiness), a pressure sensing device (e.g., subject 12 may squeeze the readiness indicator device to indicate readiness), a device configured to recognize a special breathing pattern inhaled from and/or exhaled into subject interface 16, and/or other devices. The readiness indicator device may be configured to communicate wirelessly and/or via wires with other components (e.g., processor 20) of system 10. Subject 12 may use the readiness indicator device to trigger breath stacking therapy.

Although sensors 18 are illustrated in FIG. 1 at a single location in system 10, this is not intended to be limiting. Sensors 18 may comprise sensors disposed in a plurality of locations, such as for example, at various locations within (or in communication with) conduit 40, within pressure generator 14, within (or in communication with) interface appliance 42, within (or in communication with) user interface 22, and/or other locations. In some embodiments, sensors 18 may comprise one or more stand-alone devices. For example, the readiness indicator device may be a device held by subject 12, worn by subject 12, placed in proximity to subject 12, and/or have other configurations.

Processor 20 is configured to provide information processing capabilities in system 10. As such, processor 20 may comprise one or more of a digital processor, an analog processor, a digital circuit designed to process information, an analog circuit designed to process information, a state machine, and/or other mechanisms for electronically processing information. Although processor 20 is shown in FIG. 1 as a single entity, this is for illustrative purposes only. In some implementations, processor 20 may comprise a plurality of processing units. These processing units may be physically located within the same device (e.g., pressure generator 14), or processor 20 may represent processing functionality of a plurality of devices operating in coordination.

As shown in FIG. 1, processor 20 is configured to execute one or more computer program modules. The one or more computer program modules may comprise one or more of a parameter module 50, a control module 52, an event module 54, a breath stacking module 56, and/or other modules. Processor 20 may be configured to execute modules 50, 52, 54, and/or 56 by software; hardware; firmware; some combination of software, hardware, and/or firmware; and/or other mechanisms for configuring processing capabilities on processor 20.

It should be appreciated that although modules 50, 52, 54, and 56 are illustrated in FIG. 1 as being co-located within a single processing unit, in implementations in which processor 20 comprises multiple processing units, one or more of modules 50, 52, 54, and/or 56 may be located remotely from the other modules. The description of the functionality provided by the different modules 50, 52, 54, and/or 56 described below is for illustrative purposes, and is not intended to be limiting, as any of modules 50, 52, 54, and/or 56 may provide more or less functionality than is described. For example, one or more of modules 50, 52, 54, and/or 56 may be eliminated, and some or all of its functionality may be provided by other modules 50, 52, 54, and/or 56. As another example, processor 20 may be configured to execute one or more additional modules that may perform some or all of the functionality attributed below to one of modules 50, 52, 54, and/or 56.

Parameter module 50 is configured to determine one or more parameters within system 10. The one or more parameters within system 10 may comprise gas parameters related to the pressurized flow of breathable gas, breathing parameters related to the respiration of subject 12, parameters indicating that subject 12 is ready for breath stacking therapy, and/or other parameters. Parameter module 50 is configured to determine the one or more parameters based on the output signals of sensors 18 and/or other information. The information determined by parameter module 50 may be used for controlling pressure generator 14, stored in electronic storage 24, and/or used for other uses.

The one or more gas parameters of the pressurized flow of breathable gas may comprise, for example, one or more of a pressure, a flow rate, a volume, humidity, temperature, acceleration, velocity, and/or other gas parameters. Breathing parameters related to the respiration of subject 12 may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiration frequency, and/or other breathing parameters. The parameters indicating that subject 12 is ready for breath stacking therapy may include one or more of the gas parameters, the breathing parameters, and/or other parameters. In some embodiments, the parameters indicating that subject 12 is ready for breath stacking therapy may include a level of an output signal received from the readiness indicator device, and/or other devices.

Control module 52 is configured to control pressure generator 14 to generate the flow of gas in accordance with a pressure control ventilation therapy regime. Control module 52 is configured to control pressure generator 14 based on the output signals from sensors 18, information determined by parameter module 50, information entered by a user to user interface 22, and/or other information. The pressurized flow of gas generated by pressure generator 14 is controlled to replace and/or compliment the regular breathing of subject 12. Pressure control ventilation therapy may be used to open and/or maintain an open airway in subject 12 so that oxygen and carbon dioxide may be exchanged more easily, requiring little and/or no effort from subject 12. Control module 52 may control pressure generator 14 such that a positive pressure is applied to the airway of subject 12 during inhalation and/or at other times. The level of the positive pressure may be determined based on a pressure level set by a doctor, a caregiver, subject 12, and/or other users via user interface 22; determined by control module 52 based on previous respiration of subject 12; and/or determined based on other information. During pressure control ventilation therapy, control module 52 causes pressure generator 14 to deliver the pressurized flow of breathable gas at the set pressure during inhalation while the tidal volume is allowed to vary.

By way of non-limiting example, control module 52 may control pressure generator 14 such that the pressure control ventilation therapy provided to subject 12 includes continuous mandatory ventilation (CMV), intermittent mandatory ventilation (IMV), assist controlled (AC), intermittent non-invasive positive pressure ventilation (IPPV) also known as mouth piece ventilation (MPV), and/or other types of pressure control ventilation therapy. For example, CMV delivers ventilator breaths (the pressurized flow of breathable gas) to a patient regardless of patient need and/or effort according to preset variables set by a doctor, a caregiver, the patient, and/or other users. IMV intermittently supplies ventilator breaths to the patient based on the effort and/or need of the patient. AC synchronizes the delivery of all ventilator breaths with patient inspiratory effort. IPPV utilizes a non-invasive interface (e.g., interface appliance 42) and only intermittently delivers ventilator breaths when the patient is attached to the mouthpiece.

In some embodiments, control module 52 is configured to control pressure generator 14 to generate the flow of gas in accordance with a therapy regime in addition to and/or instead of the ventilation described above. For example, control module 52 may be configured to control pressure generator 14 to generate the flow of gas in accordance with a continuous positive airway pressure support (CPAP) therapy regime, a bi-level positive airway pressure support (BPAP) therapy regime, a volume control therapy regime, and/or other pressure support therapy regimes. For example, CPAP supplies a fixed positive pressure to maintain a continuous level of positive airway pressure in a patient. BPAP provides a first inspiratory pressure (IPAP) and a second, typically lower, expiratory pressure (EPAP) for easier exhalation during ventilation.

In some embodiments, control module 52 is configured to determine the respiratory phase (e.g., inhalation, exhalation) during breathing of subject 12. The respiratory phase determinations made by module 52 are based on the output signals from sensors 18, information determined by parameter module 50, and/or other information. The respiratory phase determinations may be used by control module 52 to control pressure generator 14 to generate the pressurized flow of breathable gas delivered to subject 12, may be stored in electronic storage 24, and/or used for other uses. In some embodiments, control module 52 is configured to determine the respiratory phase (e.g., inhalation, exhalation) based on changes in pressure, flow rate, and/or other parameters determined by parameter module 50.

Event module 54 is configured to determine breath stacking events. A breath stacking event may comprise one or more of an indication from subject 12 that he or she is ready for breath stacking (e.g., via the readiness indicator device), a flow rate change in the pressurized flow of breathable gas of some amount, a lack of flow rate change of some amount, the absence of expired volume in the breathing circuit, a lack of pressure and/or volume in the airway of subject 12 until expiration of a monitored period of time (e.g., if subject 12 does not exhale), one or more user setting changes (e.g., subject 12 increasing the applied pressure of the pressure control therapy regime via user interface 22), a pre-programmed prompt from processor 20 (e.g., if breath stacking therapy is implemented on a prescheduled basis), direct input from sensors 18 (e.g., a button, a switch, a camera, a microphone, a motion sensing device, a pressure sensing device, etc.), and/or other breath stacking events. A breath stacking event may comprise an instantaneous occurrence (e.g. the indication from subject 12 via the readiness indicator device), and/or conditions/circumstances that last for a period of time (e.g., subject 12 does not exhale between breaths such that the pressure is maintained in the airway of subject 12).

Event module 54 is configured to determine breath stacking events responsive to the output signals and/or the determined parameters indicating that the subject is ready to receive breath stacking therapy, and/or based on other information. In some embodiments, the breath stacking events are determined based on a single output signal and/or parameter. For example, event module 54 may determine a breath stacking event responsive to an output signal from the readiness indicator device indicating that subject 12 is ready for breath stacking. In some embodiments, the breath stacking events are determined based on a combination of one or more of the output signals and/or one or more of the determined parameters. For example, parameters indicating that subject 12 is ready for breath stacking may be a combination of one or more of the gas parameters and/or the breathing parameters. A constant pressure of the gas in the airway of subject 12 held for a predetermined amount of time may indicate that subject 12 is ready for breath stacking therapy.

In some embodiments, event module 54 is configured such that indicating that the subject is ready to receive breath stacking therapy includes the output signals and/or the determined parameters breaching threshold levels. In some embodiments, the threshold levels for the output signals and/or the parameters may be determined based on previous respiration of subject 12, based on information entered and/or selected by a user via user interface 22, and/or based on other information. Users may include doctors, caregivers, subject 12, and/or other users. By way of a non-limiting example, a user may enter and/or select, via user interface 22, a threshold pressure level and a threshold amount of time.

Event module 54 may determine a breath stacking event responsive to the pressure level of the gas in the airway of subject 12 remaining above the entered pressure threshold level for the entered threshold amount of time (e.g., indicating that subject 12 has not exhaled and is ready for breath stacking therapy). Other examples of parameters that may be compared to threshold levels to indicate that subject 12 is ready for breath stacking therapy may include parameters related to a button (e.g. an electrical signal), a camera (e.g., a reference image), a microphone (e.g., a sound level), a motion sensing device (e.g., a specific gesture such as a wave), a pressure sensing device (e.g., subject 12 may squeeze the readiness indicator device with a given force to indicate readiness), a device configured to recognize a special breathing pattern inhaled from and/or exhaled into subject interface 16 (e.g., a series of pressure levels and/or flow rates), and/or other parameters.

Breath stacking module 56 is configured to, responsive to the determination of a breath stacking event, control pressure generator 14 to generate the pressurized flow of breathable gas according to a breath stacking therapy regime. Breath stacking module 56 is configured to control pressure generator 14 to generate the pressurized flow of breathable gas according to the breath stacking therapy regime during a current inhalation of subject 12 that follows the breath stacking event determination. Breath stacking module 56 is configured such that controlling pressure generator 14 to generate the pressurized flow of breathable gas according to the breath stacking therapy regime comprises controlling pressure generator 14 to generate the pressurized flow of breathable gas during the current inhalation at a second pressure level that is higher than a first pressure level of the pressurized flow of breathable gas generated during an immediately previous inhalation of subject 12.

In some embodiments, responsive to individual breath stacking events being determined prior to each breath in a series of successive breaths, breath stacking module 56 is configured to control pressure generator 14 to generate the pressurized flow of breathable gas during the current inhalation in the series of successive breaths at a pressure level that is higher than the immediately previous breath stacked pressure level.

In some embodiments, responsive to a single breath stacking event determination, breath stacking module 56 may be configured to control pressure generator 14 to increase the pressure level of the pressurized flow of breathable gas for each inhalation in a series of one or more subsequent inhalations (relative to the immediately previous inhalation in the series of subsequent inhalations) without additional breath stacking event determinations. The number of inhalations in the series of subsequent inhalations may be programmed at manufacture, determined based on previous respiration of subject 12, determined based on information received via user interface 22, and/or determined based on other information.

In some embodiments, breath stacking module 56 is configured such that the increased pressure level(s) (e.g., the second pressure level) are higher than the immediately previous pressure level(s) (e.g., the first pressure level) by a predetermined amount. The predetermined amount may be programmed at manufacture, set by a doctor, set by a caregiver, set by subject 12, and/or set by other users via user interface 22, and/or be determined via other methods. In some embodiments, the predetermined amount may be constant. In some embodiments, such as during breath stacking therapy for a series of consecutive breaths, the predetermined amount may ramp such that the initial pressure increases are large but then get smaller as each successive breath in the series of breaths is stacked.

Figure 2A:
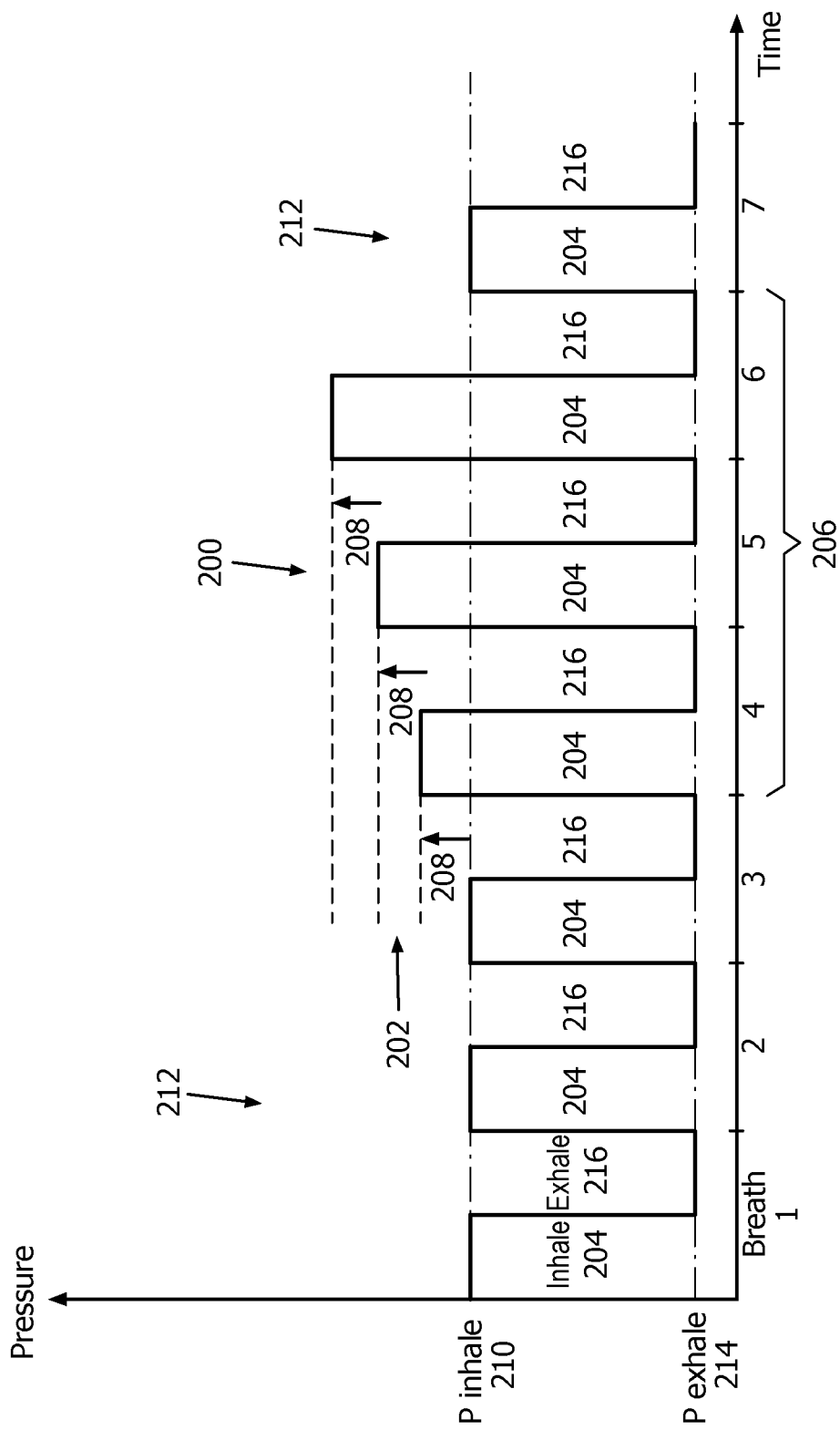
FIG. 2A illustrates breath stacking therapy wherein the increased pressure levels during inhalation for a series of consecutive breaths are higher than the immediately previous pressure levels by a constant amount.

For example, FIG. 2A illustrates breath stacking therapy 200 wherein the increased pressure levels 202 during inhalation 204 for a series of consecutive breaths 206 are higher than the immediately previous pressure levels by a constant amount 208. FIG. 2A illustrates consecutive breaths 206 corresponding to breaths 4, 5, and 6 during pressure control ventilation therapy of a subject (breaths 1-7 are illustrated). Breath stacking therapy 200 may be responsive to the determination of a breath stacking event just prior to breath 4 and/or individual breath stacking events determined just prior to breaths 4, 5, and 6. The pressure level during inhalation ($P_{inhale}$) 210 remains substantially constant during the period of pressure control ventilation 212 before and/or after breath stacking therapy 200. The pressure level during exhalation ($P_{exhale}$) 214 may have any value that is appropriate for pressure control ventilation therapy. For example, $P_{exhale}$ 214 may have a positive value, a negative value, and/or may be zero. In some embodiments, $P_{exhale}$ may be the same as $P_{inhale}$ 210.

Figure 2B:
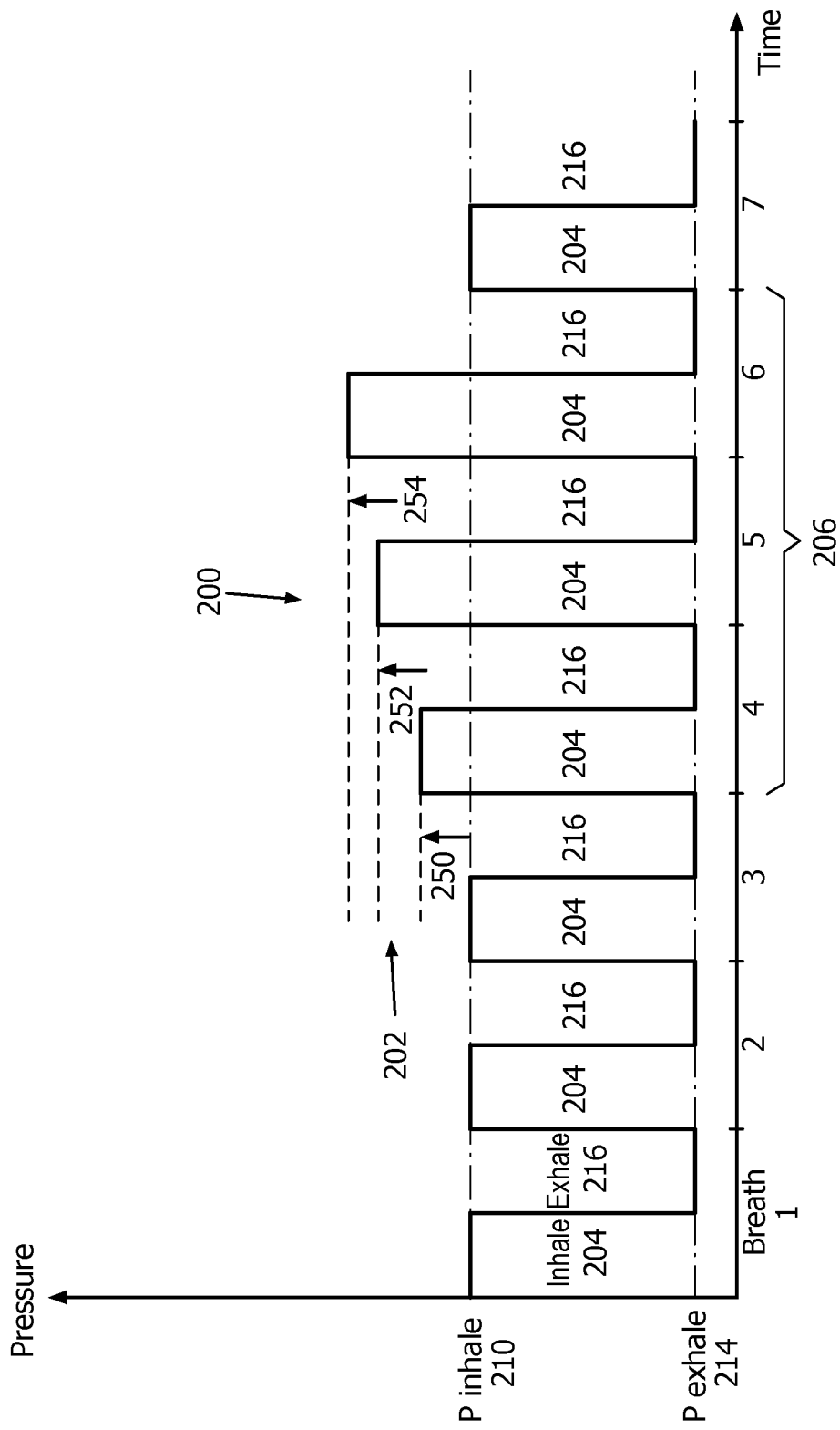
FIG. 2B illustrates breath stacking therapy wherein the increased pressure levels during inhalation for a series of consecutive breaths are higher than the immediately previous pressure levels by ramped amounts.

FIG. 2B illustrates breath stacking therapy 200 wherein the increased pressure levels 202 during inhalation 204 for a series of consecutive breaths 206 are higher than the immediately previous pressure levels by ramped amounts 250, 252, and 254. The increased pressure levels 202 ramp such that the initial pressure increase 250 is larger than the second pressure increase 252, which is again larger than the third pressure increase 254. The ramped breath stacking therapy 200 may be responsive to the determination of a breath stacking event just prior to breath 4 and/or individual breath stacking events determined just prior to breaths 4, 5, and 6.

Returning to FIG. 1, in some embodiments, breath stacking module 56 is configured to determine the increased pressure level(s) (e.g., the second pressure level) based on the output signals, the parameters determined by parameter module 50, and/or based on other information. For example, breath stacking module 56 may be configured to assess the lung compliance of subject 12 (e.g., via the output signals and/or the determined parameters) and set the pressure increase(s) to target a given tidal volume based on the lung compliance. The given tidal volume target may be programmed at manufacture, determined based on previous respiration of subject 12, determined based on information received via user interface 22, and/or determined based on other information.

As another example, breath stacking module 56 may be configured to determine the pressure increase(s) based on output signals and/or determined parameters indicating end-tidal CO2 levels. Breath stacking module 56 may be configured to adjust the pressure increase(s) based on an end tidal CO2 level relative to an end tidal CO2 threshold level. The end tidal CO2 threshold level may be programmed at manufacture, determined based on previous respiration of subject 12, determined based on information received via user interface 22, and/or determined based on other information. As a third example, breath stacking module 56 may be configured to adjust the pressure increase(s) based on oxygen saturation. Breath stacking module 56 may be configured to assess oxygen saturation (e.g., via the output signals and/or the determined parameters) and set the pressure increase(s) to target a given oxygen saturation.

In some embodiments, breath stacking module 56 is configured to limit the breath stacking therapy pressure level(s) to a maximum pressure level. Breath stacking module 56 is configured to limit the breath stacking therapy pressure level(s) to the maximum pressure level to protect subject 12. The maximum pressure level may be programmed at manufacture; determined by breath stacking module 56 based on the output signals, the parameters determined by parameter module 50, previous respiration of subject 12, and/or other information; set by a doctor, a caregiver, subject 12, and/or other users; and/or determined based on other information. Breath stacking module 56 is configured to limit the breath stacking therapy pressure level(s) to the maximum pressure level regardless of continued breath stacking event determinations.

In some embodiments, breath stacking module 56 is configured such that controlling pressure generator 14 to generate the pressurized flow of breathable gas according to the breath stacking therapy regime comprises controlling pressure generator 14 to generate a predetermined volume of gas for inhalation by subject 12 during the current inhalation. The predetermined volume of gas may be programmed at manufacture; determined by breath stacking module 56 based on the output signals, the parameters determined by parameter module 50, previous respiration of subject 12, and/or other information; set by a doctor, a caregiver, subject 12, and/or other users; and/or determined based on other information.

In some embodiments, breath stacking module 56 may be configured such that breath stacking therapy may be enabled and/or disabled by a user (e.g., a doctor, a caregiver, subject 12, and/or other users) via user interface 22. For example, breath stacking module 56 may be configured such that entries and/or selections may by a user via user interface 22 enable and/or disable breath stacking therapy. In some embodiments, breath stacking module 56 may be configured to enable and/or disable breath stacking therapy automatically. Breath stacking module 56 may be configured to enable and/or disable breath stacking therapy based on the output signals, the parameters determined by parameter module 50, previous respiration of subject 12, and/or other information. For example, based on the output signals, breath stacking module may determine that breath stacking therapy may be deleterious to subject 12 during a given pressure control ventilation therapy session and disable the ability of subject 12 to trigger breath stacking therapy via the readiness indicator device.

In some embodiments, breath stacking module 56 is configured to control pressure generator 14 to generate the pressurized flow of breathable gas according to a breath stacking therapy regime on a scheduled basis, regardless of the determination of breath stacking events. The schedule may be set by a doctor, a caregiver, subject 12, and/or other users via user interface 22, for example.

In some embodiments, breath stacking module 56 is configured to indicate to subject 12 via user interface 22 that he or she should trigger the breath stacking therapy via the readiness indicator device. Breath stacking module 56 is configured to indicate to the subject 12 that he or she should trigger the breath stacking therapy based on the output signals, the determined parameters, and/or other information.

User interface 22 is configured to provide an interface between system 10 and subject 12 and/or other users through which subject 12 and/or other users may provide information to and receive information from system 10. As described above, other users may comprise, for example, a caregiver, a doctor, and/or other users. This enables data, cues, results, and/or instructions and any other communicable items, collectively referred to as "information," to be communicated between a user (e.g., subject 12) and one or more of pressure generator 14, processor 20, and/or other components of system 10. For example, a user may specify the breath stacking therapy pressure level increases, the maximum breath stacking therapy pressure level, whether breath stacking therapy is enabled and/or disabled, and/or other information via user interface 22. As another example, breath stacking therapy frequency, therapy pressures, gas parameters of the pressurized flow of breathable gas, breathing parameters of subject 12, and/or other information may be displayed to a user (e.g., subject 12) via user interface 22.

Examples of interface devices suitable for inclusion in user interface 22 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 22 comprises a plurality of separate interfaces. In one embodiment, user interface 22 comprises at least one interface that is provided integrally with pressure generator 14.

It is to be understood that other communication techniques, either hard-wired or wireless, are also contemplated by the present disclosure as user interface 22. For example, the present disclosure contemplates that user interface 22 may be integrated with a removable storage interface provided by electronic storage 24. In this example, information may be loaded into system 10 from removable storage (e.g., a smart card, a flash drive, a removable disk, etc.) that enables the user(s) to customize the implementation of system 10. Other exemplary input devices and techniques adapted for use with system 10 as user interface 22 comprise, but are not limited to, an RS-232 port, RF link, an IR link, modem (telephone, cable or other). In short, any technique for communicating information with system 10 is contemplated by the present disclosure as user interface 22.

In some embodiments, electronic storage 24 comprises electronic storage media that electronically stores information. The electronic storage media of electronic storage 24 may comprise one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 24 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 24 may store software algorithms, information determined by processor 20, information received via user interface 22, and/or other information that enables system 10 to function properly. Electronic storage 24 may be (in whole or in part) a separate component within system 10, or electronic storage 24 may be provided (in whole or in part) integrally with one or more other components of system 10 (e.g., user interface 22, processor 20, etc.).

Information determined by processor 20 and/or stored by electronic storage 24 may include information related to breath stacking therapy (e.g., frequency of breath stacking therapy), information related to pressure control ventilation therapy, and/or other information. The information stored by electronic storage 24 may be viewed via user interface 22, by connecting (wired and/or wireless) electronic storage 24 to a separate computer, and/or other via other methods. The information stored by electronic storage 24 may be used, for example, to adjust breath stacking therapy settings, used by a doctor to make medical decisions, and/or for other uses.

Figure 3:
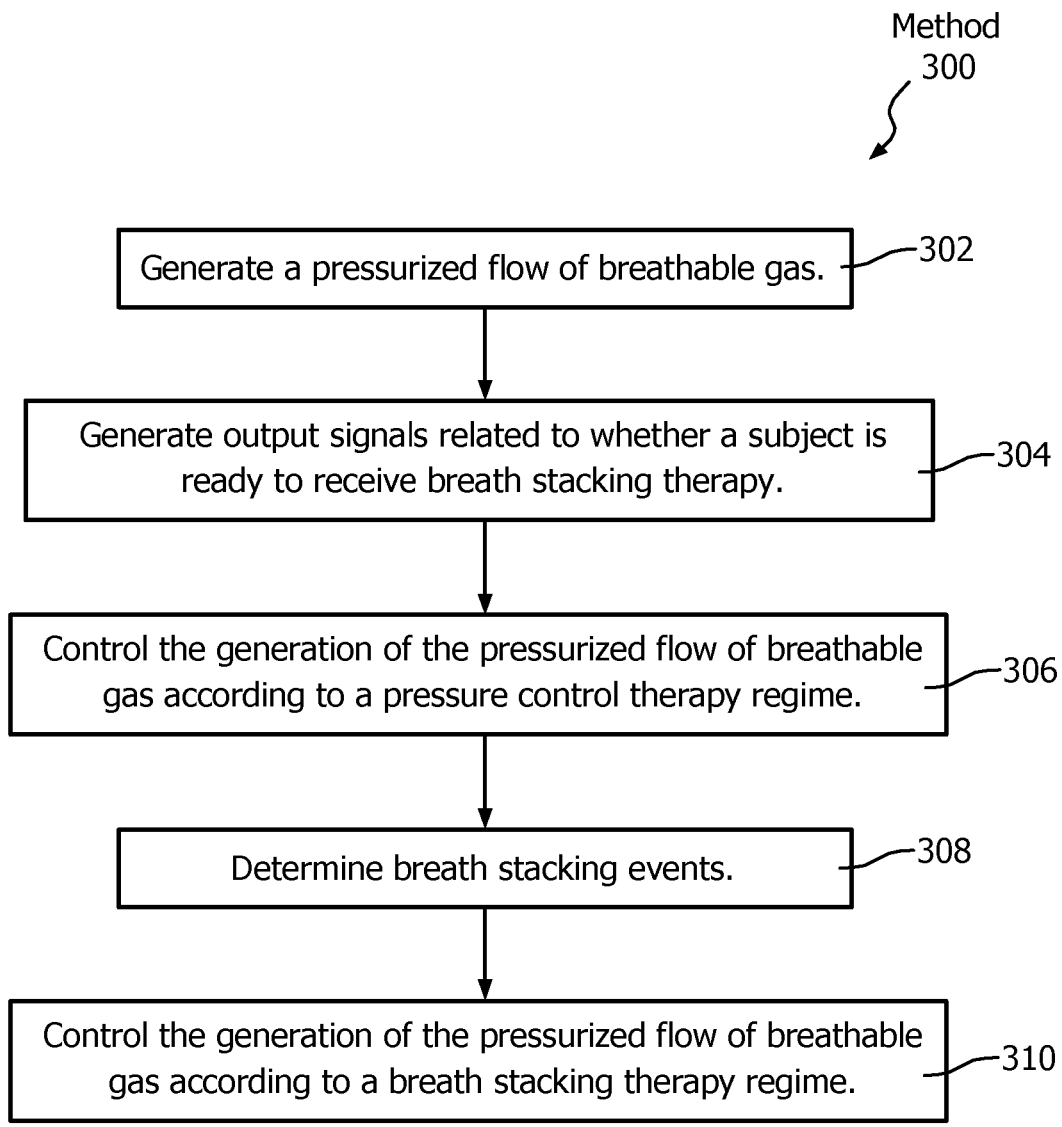
FIG. 3 is a method of delivering a pressurized flow of breathable gas to the airway of a subject.

FIG. 3 illustrates a method 300 of delivering a pressurized flow of breathable gas to the airway of a subject with a pressure support system. The system includes a pressure generator, one or more sensors, one or more processors, and/or other components. The operations of method 300 presented below are intended to be illustrative. In some embodiments, method 300 may be accomplished with one or more additional operations not described, and/or without one or more of the operations discussed. Additionally, the order in which the operations of method 300 are illustrated in FIG. 3 and described below is not intended to be limiting.

In some embodiments, method 300 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 300 in response to instructions stored electronically on an electronic storage medium. The one or more processing devices may include one or more devices configured through hardware, firmware, and/or software to be specifically designed for execution of one or more of the operations of method 300.

At an operation 302, the pressurized flow of breathable gas is generated with the pressure generator. In some embodiments, operation 302 is performed by a pressure generator the same as or similar to pressure generator 14 (shown in FIG. 1 and described herein).

At an operation 304, one or more output signals conveying information related to whether the subject is ready to receive breath stacking therapy are generated with the one or more sensors. In some embodiments, the one or more sensors may include a readiness indicator device that is configured to receive an indication from the subject that the subject is ready to receive breath stacking therapy. In some embodiments, operation 304 is performed by sensors the same as or similar to sensors 18 (shown in FIG. 1 and described herein).

At an operation 306, the pressure generator is controlled to generate the pressurized flow of breathable gas according to a pressure control therapy regime. In some embodiments, operation 306 is performed by a computer program module the same as or similar to control module 52 (shown in FIG. 1 and described herein.)

At an operation 308, breath stacking events are determined. The breath stacking events are determined responsive to the output signals indicating that the subject is ready to receive breath stacking therapy. In some embodiments, operation 308 is performed by a computer program module the same as or similar to event module 54 (shown in FIG. 1 and described herein).

At an operation 310, the pressure generator is controlled to generate the pressurized flow of breathable gas according to a breath stacking therapy regime. The pressure generator is controlled to generate the pressurized flow of breathable gas according to the breath stacking regime responsive to the determination of a breath stacking event. The pressure generator is controlled to generate the pressurized flow of breathable gas according to the breath stacking therapy regime during a current inhalation of the subject following the breath stacking event determination.

In some embodiments, controlling the pressure generator to generate the pressurized flow of breathable gas according to the breath stacking therapy regime comprises controlling the pressure generator to generate the pressurized flow of breathable gas during the current inhalation at a second pressure that is higher than a first pressure of the pressurized flow of breathable gas generated during an immediately previous inhalation of the subject. The second pressure may be determined based on the output signals, may be a predetermined pressure, and/or may be determined by other methods. In some embodiments, controlling the pressure generator to generate the pressurized flow of breathable gas according to the breath stacking therapy regime comprises controlling the pressure generator to generate a predetermined volume of gas for inhalation by the subject during the current inhalation. In some embodiments, operation 310 is performed by a computer program module the same as or similar to breath stacking module 56 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A pressure support system configured to deliver a pressurized flow of breathable gas to the airway of a subject, the pressure support system comprising:

a pressure generator configured to generate the pressurized flow of breathable gas;

one or more sensors configured to generate output signals conveying information related to whether the subject is ready to receive a breath stacking therapy; and one or more processors configured to execute computer program modules, the computer program modules comprising:

a control module configured to control the pressure generator to generate the pressurized flow of breathable gas according to a pressure control therapy regime, an event module configured to determine breath stacking events responsive to the output signals indicating that the subject is ready to receive the breath stacking therapy, and a breath stacking module configured to, responsive to the determination of a breath stacking event, control the pressure generator to generate the pressurized flow of breathable gas so as to provide the breath stacking therapy, wherein the breath stacking therapy includes increasing a pressure of the flow of breathable gas for each inhalation in a series of inhalations such that a subsequent inhalation has a higher pressure than an immediately previous inhalation in the series of subsequent inhalations and wherein such increases in pressure in the series of subsequent inhalations occur regardless of the monitored condition of the user, wherein the breath stacking module is configured to, responsive to the determination of a breath stacking event, determine a set sequence of pressure increase amounts for the pressure in the series of subsequent inhalations and a finite number of inhalations in the series of subsequent inhalations, based on information in the output signals from previous respiration of the subject.

2. The system of claim 1, wherein the one or more sensors include a readiness indicator device configured to receive an indication from the subject that the subject is ready to receive breath stacking therapy.

3. The system of claim 1, wherein the set sequence of pressure increase amounts for the pressure in the series of subsequent inhalations:

(1) is constant; or (2) ramps such that pressure increases become smaller as each inhalation in the series of subsequent inhalations is stacked; and (3) is determined based on a lung compliance and/or end tidal CO2 from previous respiration of the subject.

4. A method of generating a pressurized flow of breathable gas for delivery to the airway of a subject with a pressure support system, the pressure support system comprising a pressure generator, one or more sensors, and one or more processors configured to execute computer program modules, the computer program modules comprising a control module, an event module, and a breath stacking module, the method comprising:

generating the pressurized flow of breathable gas with the pressure generator;

generating, with the one or more sensors, output signals conveying information related to whether the subject is ready to receive a breath stacking therapy;

controlling, with the control module, the pressure generator to generate the pressurized flow of breathable gas according to a pressure control therapy regime;

determining, with the event module, breath stacking events responsive to the output signals indicating that the subject is ready to receive the breath stacking therapy;

responsive to the determination of a breath stacking event, controlling the pressure generator, with the breath stacking module, to generate the pressurized flow of breathable gas according to the breath stacking therapy, wherein the breath stacking therapy includes increasing a pressure of the flow of breathable gas for each inhalation in a series of inhalations such that a subsequent inhalation has a higher pressure than an immediately previous inhalation in the series of subsequent inhalations, and wherein such increases in pressure in the series of subsequent inhalations occur regardless of the monitored condition of the user; and determining, responsive to the determination of a breath stacking event, a set sequence of pressure increase amounts for the pressure in the series of subsequent inhalations and a finite number of inhalations in the series of subsequent inhalations, based on information in the output signals from previous respiration of the subject.

5. The method of claim 4, further comprising generating the output signals with a readiness indicator device that is configured to receive an indication from the subject that the subject is ready to receive the breath stacking therapy.

6. The method of claim 4, wherein the set sequence of pressure increase amounts for the pressure in the series of subsequent inhalations:

(1) is constant; or
(2) ramps such that pressure increases become smaller as each inhalation in the series of subsequent inhalations is stacked; and
(3) is determined based on a lung compliance and/or end tidal CO2 from previous respiration of the subject.

7. A pressure support system configured to deliver a pressurized flow of breathable gas to the airway of a subject, the pressure support system comprising:

means for generating the pressurized flow of breathable gas;

means for generating output signals conveying information related to whether the subject is ready to receive a breath stacking therapy;

means for controlling the means for generating the pressurized flow of breathable gas to generate the pressurized flow of breathable gas according to a pressure control therapy regime;

means for determining breath stacking events responsive to the output signals indicating that the subject is ready to receive the breath stacking therapy; and responsive to the determination of a breath stacking event, means for controlling the means for generating the pressurized flow of breathable gas to generate the pressurized flow of breathable gas according to the breath stacking therapy, wherein the breath stacking therapy includes increasing a pressure of the flow of breathable gas for each inhalation in a series of inhalations such that a subsequent inhalation has a higher pressure than an immediately previous inhalation in the series of subsequent inhalations, and wherein such increases in pressure in the series of subsequent inhalations occur regardless of the monitored condition of the user, wherein the means for controlling the means for generating the pressurized flow of breathable gas to generate the pressurized flow of breathable gas according to the breath stacking therapy determines, responsive to the determination a breath stacking event, a set sequence of pressure increase amounts for the pressure in the series of subsequent inhalations and a finite number of inhalations in the series of subsequent inhalations, based on information in the output signals from previous respiration of the subject.

8. The system of claim 7, wherein the means for generating the output signals include a readiness indicator device that is configured to receive an indication from the subject that the subject is ready to receive the breath stacking therapy.

9. The system of claim 7, wherein the set sequence of pressure increase amounts for the pressure in the series of subsequent inhalations:

(1) is constant; or
(2) ramps such that pressure increases become smaller as each inhalation in the series of subsequent inhalations is stacked; and
(3) is determined based on a lung compliance and/or end tidal CO2 from previous respiration of the subject.

* * * * *